United States Patent [19]
Koger et al.

[11] Patent Number: 6,019,727
[45] Date of Patent: Feb. 1, 2000

[54] CENTER CONDUCTOR AND PZT BONDING TECHNIQUE

[75] Inventors: James D. Koger, Santa Cruz; Anthony J. Pantages, Los Altos, both of Calif.

[73] Assignee: SCIMED Life Systems, Inc., Natick, Mass.

[21] Appl. No.: 09/127,995

[22] Filed: Jul. 31, 1998

[51] Int. Cl.[7] .............................. A61B 8/14; H04R 17/00
[52] U.S. Cl. ..................... 600/459; 600/466; 600/467; 29/25.35
[58] Field of Search .................... 600/459, 447, 600/463, 466, 467, 472; 310/348, 346, 365, 327; 367/140, 152, 155, 162; 73/642; 29/25.35

[56] References Cited

U.S. PATENT DOCUMENTS

| | | | |
|---|---|---|---|
| 5,175,709 | 12/1992 | Slayton et al. | 367/90 |
| 5,381,385 | 1/1995 | Greenstein | 367/140 |
| 5,511,296 | 4/1996 | Dias et al. | 29/25.35 |
| 5,617,865 | 4/1997 | Palczewska et al. | 600/459 |
| 5,655,276 | 8/1997 | Pattanayak et al. | 29/25.35 |
| 5,701,901 | 12/1997 | Lum et al. | 600/462 |
| 5,906,580 | 5/1999 | Kline-Schoder et al. | 600/459 |
| 5,920,972 | 7/1999 | Palczewska et al. | 29/25.35 |

*Primary Examiner*—Francis J. Jaworski
*Assistant Examiner*—Ali M. Imam
*Attorney, Agent, or Firm*—Townsend and Townsend and Crew LLP

[57] ABSTRACT

A transducer assembly having an improved external connection configuration, a method for manufacturing such a transducer assembly, and a catheter system incorporating the transducer assembly. The improved connection configuration is achieved by creating a conductive path from an upper electrode of the transducer to an upper surface of the transducer assembly so that an external electrical lead can be attached to the active portion of the transducer element via the path.

20 Claims, 5 Drawing Sheets

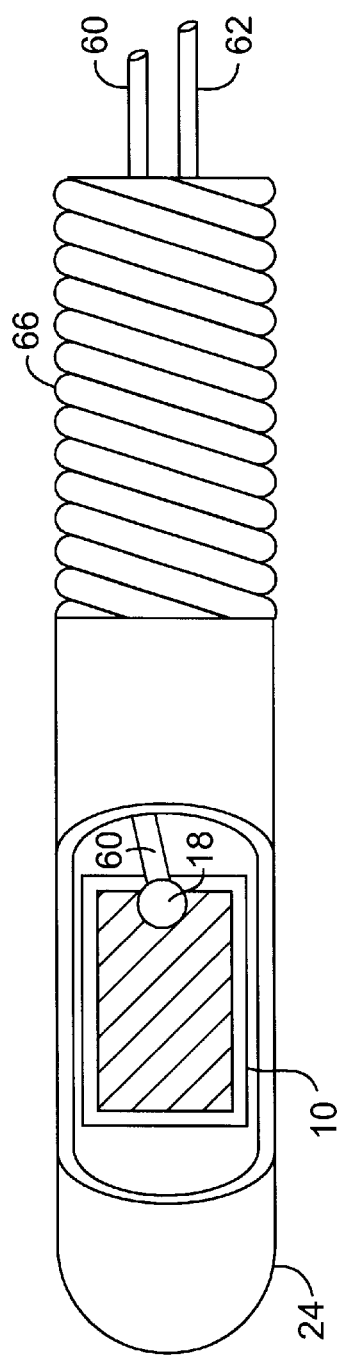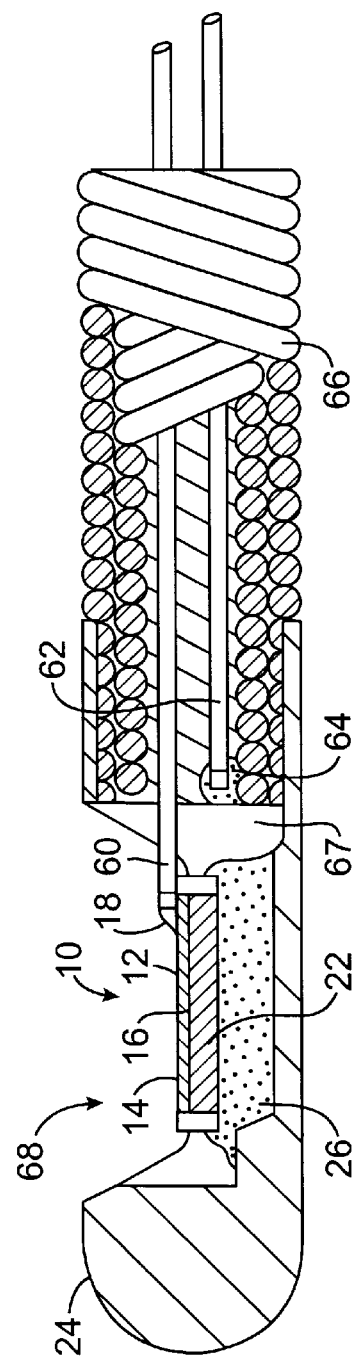
FIG. 1A (PRIOR ART)
FIG. 1B (PRIOR ART)

CENTER CONDUCTOR AND PZT BONDING TECHNIQUE

BACKGROUND OF THE INVENTION

1. Field of the Invention

The present invention relates generally to medical devices and methods for their fabrication. In particular, the invention relates to a transducer which has an improved external connection configuration for making an electrical connection to an imaging catheter.

2. Description of the Relevant Art

Intravascular imaging catheters, generally include one or more ultrasonic transducers which are capable of generating a high-frequency electrical signal, on the order of 30 MHZ, which is used to generate an image. The transducers may be front looking i.e. axially mounted so that an ultrasonic pulse is transmitted principally along the catheter axis, or side-looking i.e. mounted so that an ultrasonic pulse is transmitted in a direction perpendicular to the catheter axis.

In one example, a rotatable, side-looking ultrasonic transducer assembly 10, as shown in FIGS. 1A–1C, includes a single transducer element 12. The function of transducer element 12 is to produce and receive an ultrasonic beam. The beam is projected radially outward, normal to the surface of transducer element 12. Transducer element 12 is then rotated about an axis of the vessel to scan the interior of the blood vessel wall. Transducer element 12 detects reflections of the beam from the vessel wall which are converted to a cross-sectional image of the vessel.

Transducer element 12 is typically configured as a thin, rectangular sheet, which is fabricated from a piezoelectric material. Front and back surfaces of transducer element 12 are covered with thin film electrodes 14 and 16, respectively. As is well known, when a voltage is applied to electrodes 14 and 16, transducer element 12 vibrates to generate pulses at a resonant frequency determined by the mechanical and piezoelectric properties of transducer assembly 10. Conversely, when transducer assembly 10 receives an ultrasonic pulse, an imaging signal, in the form of a voltage pulse, is generated on electrodes 14 and 16 which may be amplified and transmitted to a video or other image generating system.

The external connection of leads to transducer assembly 10 to a lead 60, as shown in FIG. 1C, is of particular interest to the present invention. Lead 60 is coupled to the upper electrode 14 using a manually applied, conductive adhesive 18, usually an epoxy bond formulation including silver. The conductive epoxy 18 provides both a bond and an electrical path from the lead to upper electrode 14. In most cases, a matching layer 15, is formed over the upper electrode 14 prior to connecting external lead 60. In such cases, matching layer 15 must be formed from an electrically conducting material in order to provide the necessary conductive path between lead 60 and upper electrode 14.

Referring again to FIG. 1B, transducer element 12 is mounted within a receptacle 68 formed in a rotatable housing 24 using a bed of conductive adhesive filler 26. A second lead 62 is coupled to housing 24 which is electrically grounded to electrode 16 through the conductive adhesive filler 26. In this way, electrical connections to both electrodes 14 and 16 can be brought out through leads 60 and 62, respectively.

To form high-quality intravascular images, the active surface of the upper electrode 14, with or without matching layer 15 in place, should be kept relatively free of obstructions. The above-described external connection configuration has been successfully implemented in transducer assemblies that are used in relatively large diameter catheters. The presence of epoxy bond material 18 over the active surface of transducer element 12 has not typically interfered with image quality since the surface area occupied by bond material 18 is small relative to the remaining surface area of active transducer element 12 available for transmission and reception. Accordingly, preciseness and consistency in sizing and locating of the epoxy bond on the transducer element surface during assembly has been of minor importance.

To access small coronary and other arteries, however, "low profile" catheters must be used. These catheters have small diameters, which require the use of smaller transducer assemblies which have correspondingly smaller active surface areas. As the transducer element size is reduced, the relative space available on the active surface for external connection is substantially diminished. As the bond material occupies a proportionately larger amount of the available active surface area, aperture and resolution can be lost, thereby degrading the image and its usefulness. This, in turn, increases the importance of making smaller, uniformly sized, and precisely located bonds.

Unfortunately, reducing the bonding area used for external connection reduces the bond strength between the lead and the transducer and renders bond characteristics, such as electrical resistance, more variable. While improving the quality of the bond would help the problem, the ability of technicians to make smaller, consistently sized and precisely located bonds, without sacrificing the strength and quality of the connection is limited.

Current methods for external lead connection have still other disadvantages when used with very small transducers. For example, inconsistent silver epoxy bond and matching layer ingredient formulations cause variation in transducer performance. Furthermore, state-of-the-art bonding techniques cannot be used with the above described connection configuration. For example, wire bonding, soldering, and welding techniques cannot be used to attach leads to the silver epoxy bond, matching layer, or conductive film layers. Moreover, inconsistent size and placement of the bond causes significant part-to-part variation in performance and is not suitable for producing imaging catheters with repeatable characteristics.

For these reasons it would be desirable to provide improved transducer assemblies, methods for manufacturing such assemblies, and catheter systems incorporating the assemblies, where the transducer has an improved external connection configuration which limits obstruction of the active surface of the transducer assembly. It would also be desirable to provide the such assemblies and methods having the consistent bond resistance and other improved electrical characteristics and to remove the need for using an electrically conductive epoxy bond and/or a conductive matching layer. Finally, it would also be desirable to provide methods and assemblies with consistent part-to-part transducer element performance and allow for state-of-the-art external connection bonding techniques.

SUMMARY OF THE INVENTION

The present invention provides a transducer assembly having an improved external connection configuration, a method for manufacturing such a transducer assembly, and a catheter system incorporating the transducer assembly. Generally, the improved connection configuration is achieved by creating a conductive path from an upper electrode of the transducer to an upper surface of the transducer assembly so that an external electrical lead can be attached to the active portion of the transducer element via the path. The present invention thus removes the need for using a conductive epoxy bond and/or an electrically conductive matching layer. Moreover, the improved connection may be made using smaller, uniformly sized, and precisely located bonds which creates consistent part-to-part transducer element performance and allows for producing imaging catheters with repeatable characteristics.

The improved connection configuration also significantly reduces many problems associated with the current method for externally connecting leads to the transducer element, especially the problems encountered when the method is used with very small transducers. For example, the improved connection reduces the amount of bond material obstruction of the active transducer element surface caused by excessive amounts of bond material which occupy a proportionately large amount of the available active surface area on small transducers. Moreover, the invention provides improved strength, quality and other characteristics of the bond surface, which, in turn, provide consistent electrical resistance and allows for using state-of-the-art external connection bonding techniques.

In one aspect of the invention, a method for fabricating a transducer assembly for use with an intravascular catheter, is provided which has an improved external connection configuration. The method includes providing a layer of piezoelectric material, which has a first and a second active surface. A conductive bump, preferably a gold or chrome bump, is applied to the first active surface of the piezoelectric material layer. Conductive layers are formed over the first and the second active surfaces of the piezoelectric material layer. The conductive bump is electrically coupled to the layer formed over the first active surface. An attachment surface is formed on the top of the bump. Advantageously, the top portion of the bump is ground to a predetermined depth to expose a flat, truncated portion of the bump for use as the bonding attachment surface. The transducer assembly is then cut out from the layered structure.

In another aspect, a transducer assembly for use with an intravascular imaging catheter is provided which has an active transducer element. The transducer element has oppositely facing first and second active surfaces. The assembly also has a conductive bump which is applied to the first active surface. Electrodes are formed onto the first and second active surfaces of the transducer element. The conductive bump provides an electrical path to the first electrode.

In yet another aspect, an improved ultrasonic catheter system is provided. The system is of the type which includes a transducer assembly. The assembly has an active transducer element, which has a first and a second electrode disposed on an active surface thereof. The improvement includes an electrically conductive bump disposed on an active surface of the transducer element. The bump being in direct electrical contact with the first electrode. The upper portion of the bump is adapted for connecting a lead thereto.

BRIEF DESCRIPTION OF THE DRAWINGS

FIGS. 1A and 1B are top and cross-sectional views, respectively, of the electrical connection to a standard transducer mounted in a housing.

DESCRIPTION OF THE SPECIFIC EMBODIMENT

Figure 2:
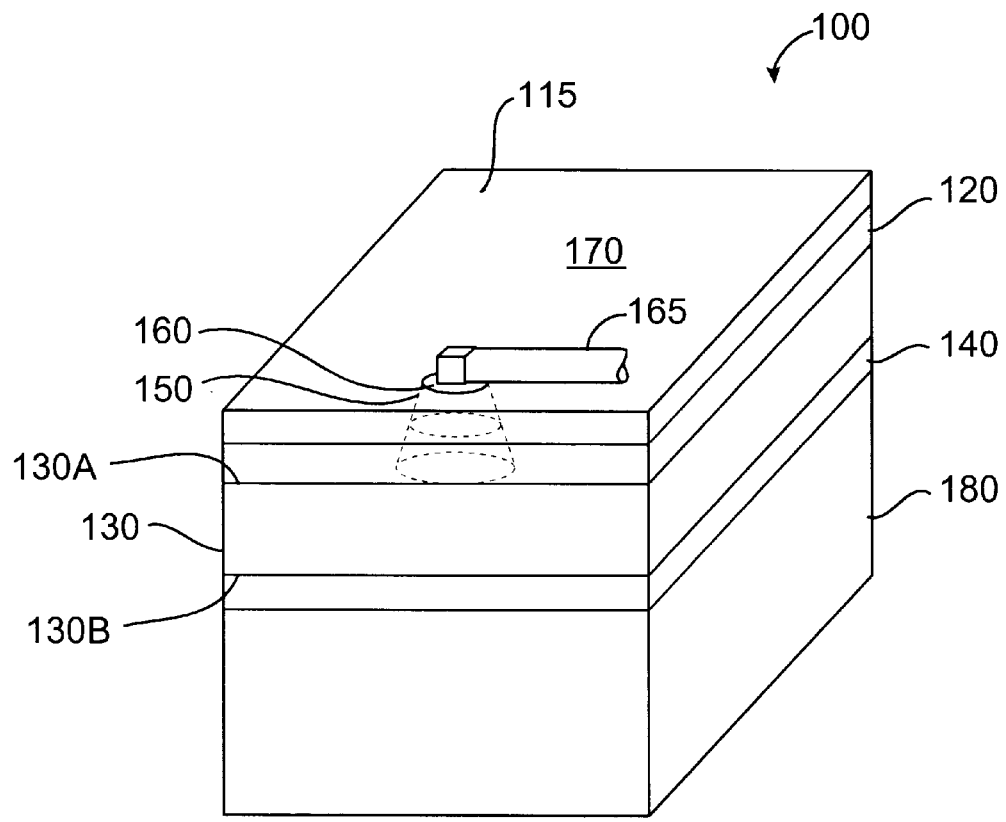
FIGS. 2 and 2A illustrate perspective views of the improved transducer assembly which has an improved external connection configuration according to the present invention.
Figure 2A:
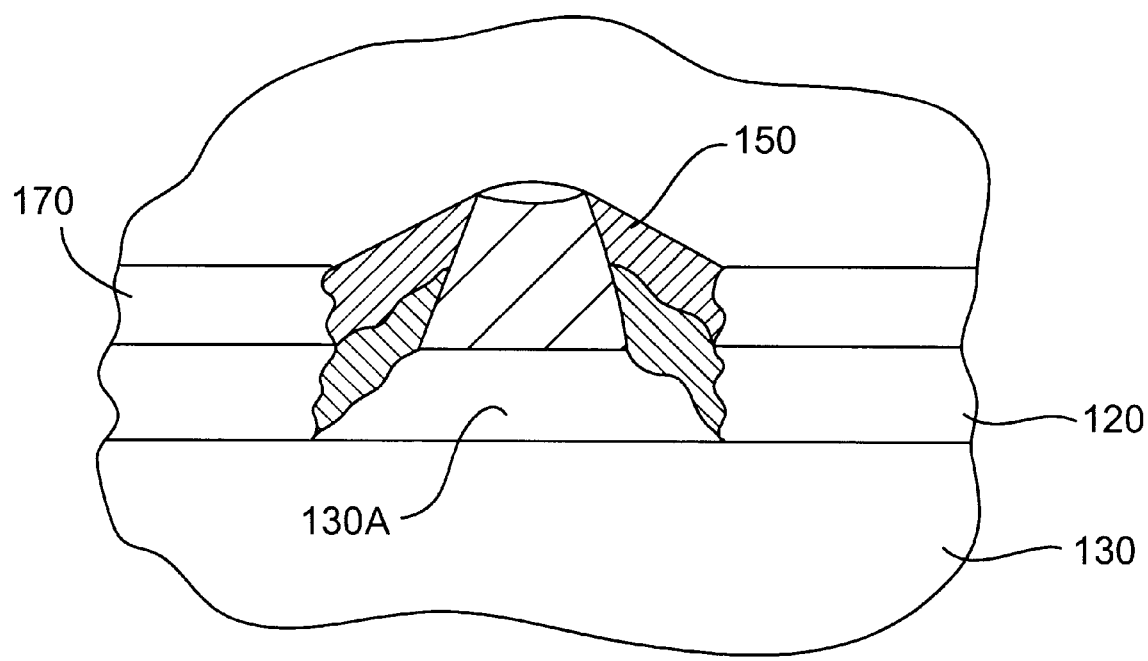

Referring now to FIGS. 2 and 2A, a transducer assembly 100 is shown with an improved external connection configuration according to the present invention. Transducer assembly 100 is typically formed as a layered structure having a piezoelectric (PZT) transducer element 130 sandwiched between other layers that electrically and acoustically interact with the transducer element. An electrically conductive bump 150 is disposed on upper surface 130A of transducer element 130. Electrodes 120 and 140 are formed over bump 150 and upper and lower active surfaces 130A and 130B of transducer element 130, typically as film layers, which are described in more detail below. Bump 150 is in direct electrical connection to the first electrode 120. Thus, bump 150 provides a direct electrical path from an electrical lead 165 through bump 150 to the first electrode 120. An attachment surface or pad 160 is created on the surface of transducer 100 by removing a top portion of bump 150 to expose a flat, smooth surface which is preferably flush with the upper surface of assembly 100. In most cases, transducer assembly 100 has a matching layer 170 formed over an upper surface of the first electrode 120 and/or a backing element 180 attached to second electrode 140. Preferably, matching layer 170 has a thickness equal to a fraction of a wavelength of the ultrasonic signal, preferably a one-quarter wavelength. Conveniently, grinding of matching layer 160 to one-quarter wavelength thickness can simultaneously truncate and expose the top portion of bump 150 which provides the attachment surface 160. Thus, the attachment surface 160 will preferably be a smooth metal surface suitable for bonding of lead 165 by various conventional joining techniques. The effective size of the exposed metallic pad can be made very small, typically, the pad may have a maximum width (usually a diameter) below 0.25 mm, preferably below 0.10 mm.

Figure 1C:
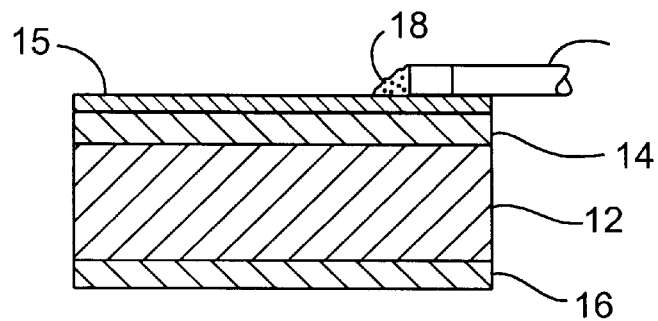
FIG. 1C is a cross-sectional view of the electrical connection to a standard transducer where the transducer has a matching layer.

Backing element 180 both attenuates ultrasonic energy from the back face of transducer assembly 100 and facilitates mounting of transducer assembly 100 in the distal housing of a catheter. For example, the transducer assembly 100 may be mounted within the receptacle 68 of a catheter, generally as shown in FIG. 1B.

Figure 3A:
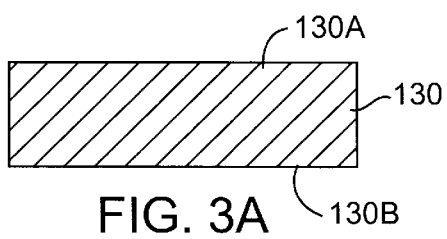
FIGS. 3A–3F show cross-sectional views of a portion of a transducer array undergoing subsequent steps in the fabrication of the transducer as in FIG. 2, with an improved external connection configuration according to the present invention.

FIGS. 3A–3F, illustrate a method for manufacturing transducers having the improved external connection configuration of the present invention. Conveniently, multiple transducers may be fabricated simultaneously from a large sheet of PZT material. As shown in FIG. 3A, the PZT material has a first active surface 130A and a second active surface 130B. The surfaces 130A and 130B face in opposite directions. For example, PZT layer 130 will typically be configured as a rectangular sheet, which may be 1.0 by 1.0 inches in size, and which can be ground or machined down to any desired thickness. Preferably, the thickness will range from 0.020 to 0.001 inches or less. The PZT layer 130 may be formed from any suitable piezoelectric material, preferably being made from conventional materials, such as PZT or other piezoceramic materials, quartz or other single crystal materials, piezocomposites, piezoelectric polymers, and magnetostrictive or piezostrictive materials.

Figure 3B:
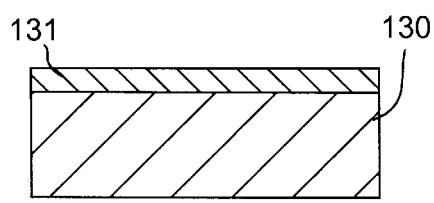

After the PZT layer 130 has been suitably formed, a plurality of conductive, metallic bumps 150 are applied to the upper surface of the PZT layer. Metallic bumps having very uniform sizes (preferably with widths varying by less than ±10%) which may be formed by well known semiconductor techniques, using commercially available equipment. Alternatively, the bumps may be applied by plating a layer 131 of a suitable metal, such as chrome or gold, over the surface 130 as shown in FIG. 3B. The layer 131 may then be etched by photolithography or other means to produce bumps 150.

Figure 3C:
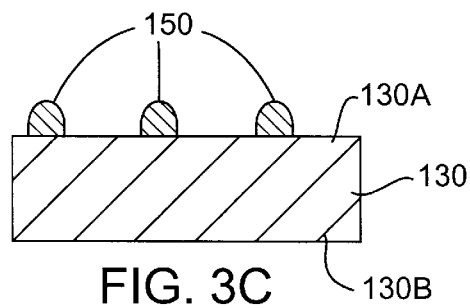

As shown in FIG. 3C, bumps 150 are positioned over surface 130A of PZT layer 130 in a prearranged pattern that permits cutting or dicing of single transducer assemblies 100 from the PZT layer (described below). The location of bump 150 is accurately registered on upper surface 130A of the PZT layer 130 to ensure that the relative locations of all bumps 150, and subsequently attachment pads 160 (FIG. 3F), are consistent on a part-to-part basis. Chrome or gold bumps are preferred since they provide consistent electrical resistance, are easy to manufacture, and provide characteristics suitable for high quality bonding.

Figure 3D:
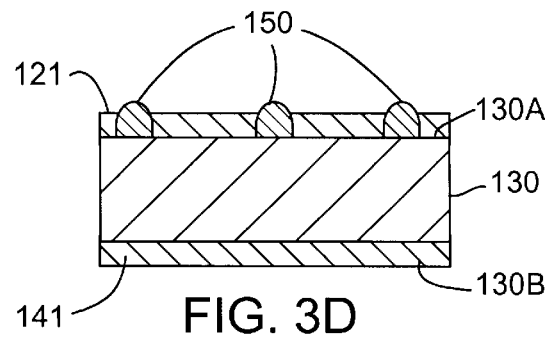

Referring now to FIG. 3D, conductive films 121 and 141 are formed over upper active surface 130A and lower active surface 130B, respectively. The conductive layers may be applied by well known fabrication techniques, such as flashing, electroplating, metallic thin-film deposition, evaporation, sputtering and the like. The films can be made of any conductive material, but preferably are made of gold or chrome, more preferably the films are the same material as the bump 150 to enhance electrical contact. The upper film 121 and lower film 141 will form the first electrode 120 and second electrode 140, respectively, when the individual assemblies 100 are diced as described before. Each first electrode 120 is formed around a bump 150 and provides the direct electrical path to first electrode 120.

Figure 3E:
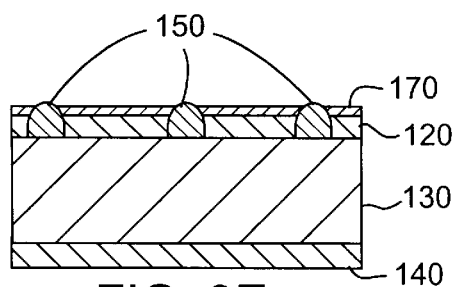

In most cases, a matching layer 170 is typically formed over first electrode 120, as is shown in FIG. 3E. The matching layer is formed from, for example, conductive epoxy, and is applied to the assembly using standard application techniques.

Figure 3F:
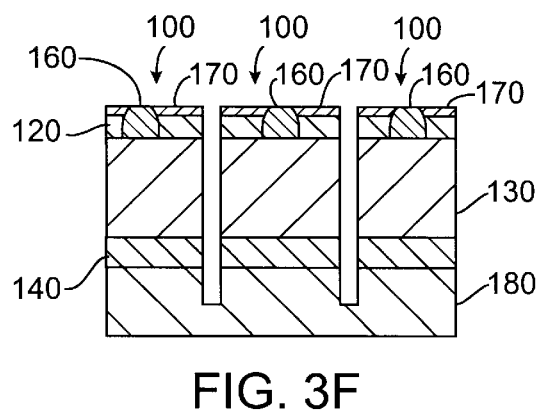

Referring now to FIG. 3F, after optionally applying non-conductive matching layer 170 to first electrode 120, the matching layer 170 is ground down, machined, or otherwise milled in such a manner that its thickness is made equal to a fraction of an ultrasonic signal wavelength emitted by the transducer, preferably one-quarter wavelength. The grinding process truncates the tops of gold bumps 150, thus forming flat attachment pads 160 on the top surface of matching layer 170. Individual transducer assemblies 100 may then be separated from the layered structure, typically by cutting or dicing. Transducer assemblies 100 can be cut into a variety of shapes, such as circular, square, rectangular, elliptical cylinders or any other suitable shape.

Figure 4:
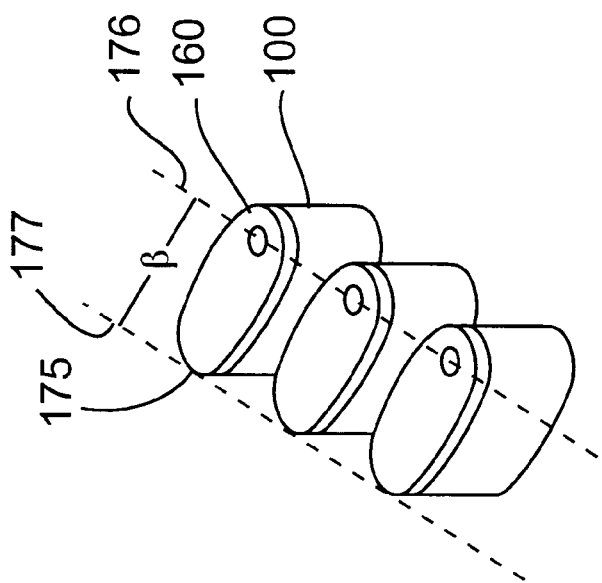
FIG. 4 illustrates a perspective view of a portion of a transducer array fabricated according to the present invention.

Upon completion of the machining process, the relative position of attachment pad 160 on the surface of transducer assembly 100, is the same between each individual transducer assembly. For example, in FIG. 4, a plurality of transducer assemblies 100 are shown each having their attachment pads 160 located along a first reference line 176. A second reference line 177 is shown along a top edge 175 of the transducer assemblies 100. The two reference lines are parallel and spaced at a distance β from each other, signifying the consistently corresponding positioning of the attachment pad 160 on the transducer assembly surface. This process provides part-to-part consistency and improved consistency of performance between transducer assemblies. Moreover, the transducer assembly processing speed is improved, since the above process may be efficiently used with automated or dexterity augmenting equipment.

After forming attachment pad 160 on the surface of transducer assembly 100, lead 165 may be bonded to the surface of pad 160 as illustrated in FIG. 2. Lead 165 can be bonded using many conventional bonding techniques, such as electric resistance spot welding, laser spot welding, or conductive epoxy, preferably, ultrasonic welding or thermosonic welding techniques are used.

Figure 5:
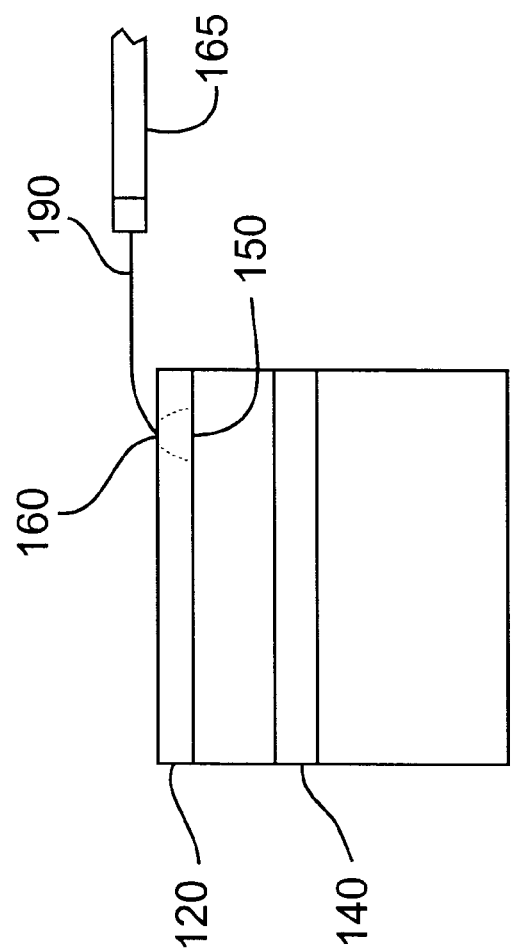
FIG. 5 illustrates a cross-sectional view of an alternative embodiment of an electrical connection according to the present invention.

In an alternative embodiment, shown in FIG. 5, a wire connector 190, preferably a gold or chrome wire, is connected to pad 160. Wire connector 190 provides an intervening connection point for lead 165. In this embodiment, lead 165 is not connected directly to transducer assembly 100, but instead is connected to wire connector 190. Advantageously, wire 190 provides for easy replacement and rebonding of lead 165, in the event that, for example, lead 165 is bonded to a defective transducer assembly.

Bonding directly to gold bump 150 or alternatively to wire connector 190 eliminates the need for a conductive epoxy bonding material for securing lead 165 (see FIG. 2 and FIG. 5) to matching layer 170. This elimination of silver epoxy material reduces the measure of obstruction of the ultrasonic signal, which is especially beneficial to small diameter transducers. Since, the attachment pad is a metal surface, other higher quality bonding techniques can be used to secure the lead to the pad and therefore to electrode 120, such as welding, soldering, and wire bonding. Also, matching layer 170, which typically supplies the conductive path from lead 165 to first electrode 120, need no longer be conductive, since gold bump 150 supplies the direct electrical path to electrode 120 in place of matching layer 170. Eliminating silver epoxy bonds and conductive silver epoxy matching layer paths, reduces variations in transducer performance. This, in turn, makes the transducer more suitable for producing imaging catheters with repeatable performance characteristics. Using non-conductive matching layers also broadens some aspects of piezoelectric material processing. Other major advantages of the improved external connection configuration include easier reworking of defective transducers and preassembly testing of the transducer while still in the "sandwich" or layered stage before the machining of individual transducers.

The invention has now been described with reference to a specific embodiment. However, the invention is not intended to be so limited. Although the invention was described as being extremely useful with small transducers, the improved external connection will work with any sized transducer assembly.

Alternatives and substitutions will also be apparent to persons of skill in the art. For example, the invention may embody a second bump disposed on second electrode 140 to provide a more direct electrical path to second electrode 140, obviating the need for conductive backing element 180. Accordingly, the invention is not intended to be limited except as provided by the appended claims.

What is claimed is:

1. A method for fabricating a transducer assembly having an improved external connection configuration for use with an intravascular catheter, said method comprising:

provi ding a layer of piezoelectric material having a first active surface and a second active surface;

applying a conductive bump to the first active surface of the piezoelectric material layer; and forming conductive layers over the first and the second active surfaces of the piezoelectric material layer, wherein the conductive bump is electrically coupled to the layer over the first active surface.

2. The method as in claim 1, further comprising forming a connective attachment surface on top of said bump; and cutting out the transducer assembly from the layered structure into one of a variety of conventional transducer assembly shapes.

3. The method as in claim 2, wherein the top portion of the bump is removed to a predetermined depth to expose a flat, truncated portion of the bump for use as the attachment surface.

4. The method as in claim 1, the method further comprising:

applying a matching layer to the first active surface of the piezoelectric layer, the matching layer surrounding the bump; and grinding the matching layer and bump to truncate and expose a top portion of the bump to provide the attachment surface.

5. The method as in claim 4, wherein the matching layer is formed to have a thickness equal to a fraction of a predetermined ultrasonic signal wavelength emitted from the first active surface.

6. The method as in claim 4, wherein applying comprises applying a matching layer made of a non-conductive material.

7. The method as in claim 1, the method further comprising bonding the second active surface to a backing element.

8. The method as in claim 1, the method further comprising attaching a lead to the connective attachment surface, wherein the attaching is accomplished by conventional bonding techniques, including wirebonding, soldering, and welding.

9. The method as in claim 1, wherein forming comprises forming a gold layer on each conductive layers.

10. The method as in claim 1, wherein providing comprises providing a piezoelectric material layer made of a material taken from the group consisting of PZT and other piezoceramic materials, quartz and other single crystal materials, piezocomposites, piezoelectric polymers, and magnetostrictive and piezostrictive materials.

11. The method as in claim 2, further comprising positioning the attachment pad in a predetermined location on the surface of the transducer assembly.

12. The method as in claim 1, wherein applying comprises applying a conductive bump made of a conductive material taken from the group comprising gold, platinum, chrome, copper, aluminum, iridium, and tungsten.

13. A transducer assembly for use with an intravascular imaging catheter, having an improved external connection configuration, the transducer assembly comprising:

a transducer element having oppositely facing first and second active surfaces;

a conductive bump applied on the first active surface of the transducer element; and electrodes formed on the first and second active surfaces of the transducer element, the conductive bump providing an electrical path to the first electrode.

14. The transducer assembly of claim 13, further comprising a matching layer formed over the first active surface of the transducer element.

15. The transducer assembly of claim 13, wherein an attachment pad is formed on a top portion of the conductive bump.

16. The transducer assembly of claim 15, wherein the bonding surface is a flat surface having a uniform diameter ranging from 0.25 mm and below.

17. The transducer assembly of claim 15, wherein a wire connector is bonded to said attachment pad to provide an intervening connection between said attachment pad and a lead.

18. The transducer assembly of claim 13, wherein the electrodes are made of gold.

19. The transducer assembly of claim 13, wherein the transducer element is a material taken from the group consisting of PZT and other piezoceramic materials, quartz and other single crystal materials, piezocomposites, piezoelectric polymers, and magnetostrictive and piezostrictive materials.

20. An improved ultrasonic catheter system of the type including a transducer assembly comprising an active transducer element having a first electrode and a second electrode on active surfaces thereof, the improvement comprising:

an electrically conductive bump disposed on an active surface of the transducer element and in a direct electrical contact with the first electrode, wherein an upper portion of the bump is adapted for connecting a lead thereto.

* * * * *